(12) United States Patent
Rodriguez, III et al.

(10) Patent No.: US 12,168,195 B2
(45) Date of Patent: Dec. 17, 2024

(54) UNIVERSAL BACTERIA FILTER APPARATUS FOR OXYGEN CONCENTRATORS

(71) Applicants: John M. Rodriguez, III, Helotes, TX (US); Alfredo Salazar, Tulsa, OK (US)

(72) Inventors: John M. Rodriguez, III, Helotes, TX (US); Alfredo Salazar, Tulsa, OK (US)

(*) Notice: Subject to any disclaimer, the term of this patent is extended or adjusted under 35 U.S.C. 154(b) by 492 days.

(21) Appl. No.: 17/534,056

(22) Filed: Nov. 23, 2021

(65) Prior Publication Data

US 2022/0168682 A1   Jun. 2, 2022

Related U.S. Application Data

(60) Provisional application No. 63/117,027, filed on Nov. 23, 2020.

(51) Int. Cl.
| | | |
|---|---|---|
| *B01D 46/00* | (2022.01) | |
| *A61M 16/10* | (2006.01) | |
| *B01D 39/16* | (2006.01) | |
| *B01D 46/52* | (2006.01) | |
| *B01D 46/62* | (2022.01) | |

(52) U.S. Cl.
CPC ........... *B01D 46/62* (2022.01); *A61M 16/101* (2014.02); *A61M 16/1055* (2013.01); *B01D 39/1623* (2013.01); *B01D 46/0004* (2013.01); *B01D 46/0008* (2013.01); *B01D 46/0028* (2013.01); *B01D 46/521* (2013.01); *B01D 2265/025* (2013.01); *B01D 2279/65* (2013.01)

(58) Field of Classification Search
CPC ................ B01D 46/62; B01D 46/0004; B01D 46/0008; B01D 46/0028; A61M 16/101; A61M 16/1055; A61M 2205/21; A61M 2205/42; A61M 2205/7518; A61M 2205/7545
USPC .................................. 55/323, 385.1; 96/121
See application file for complete search history.

(56) References Cited

U.S. PATENT DOCUMENTS

| | | | |
|---|---|---|---|
| 7,730,887 B2 * | 6/2010 | Deane ................ | A61M 16/101 128/205.12 |
| 7,833,308 B2 | 11/2010 | Amann | |
| 2005/0279212 A1 | 12/2005 | Amann | |
| 2007/0227360 A1 * | 10/2007 | Atlas .................. | A61M 16/101 96/121 |
| 2008/0087169 A1 | 4/2008 | Clark | |
| 2009/0188217 A1 * | 7/2009 | Amann ............... | B01D 46/521 55/323 |

FOREIGN PATENT DOCUMENTS

| | | | | |
|---|---|---|---|---|
| CN | 103074736 | | 5/2013 | |
| CN | 204317282 U | * | 9/2015 | ............... B07B 1/28 |

OTHER PUBLICATIONS

PCT/US2022/017047—International Search Report and Written Opinion; May 17, 2022; US.

* cited by examiner

*Primary Examiner* — Minh Chau T Pham
(74) *Attorney, Agent, or Firm* — Dennis D. Brown; Brown Patent Law, P.L.L.C.

(57) ABSTRACT

An all-in-one, universal bacteria filter apparatus which (i) can be used with oxygen concentrators produced by numerous different manufactures, (ii) can be used with concentrators of different capacities, and (iii) can be use in both vertical and horizontal orientations.

14 Claims, 4 Drawing Sheets

UNIVERSAL BACTERIA FILTER APPARATUS FOR OXYGEN CONCENTRATORS

RELATED CASE

This application claims the benefit of U.S. Provisional Patent Application Ser. No. 63/117,027 filed on Nov. 23, 2020 and incorporates said provisional application by reference into this document as if fully set out at this point.

FIELD OF THE INVENTION

The present invention is in the respiratory medical field related to oxygen concentrators. More particularly, the present invention relates to inlet air filtration apparatuses, methods, and systems for oxygen concentrators.

BACKGROUND OF THE INVENTION

Medical-related facilities and providers, including but not limited to skilled nursing care centers, home medical equipment dealers, rural hospitals, dialysis clinics, respiratory equipment dealers, medical equipment distributors, and cardiac specialty clinics, as well as many individual patients, own and use oxygen concentrators for respiratory purposes. The oxygen concentrators purchased by such institutions, companies, and individuals are produced by numerous different manufactures. However, regardless of the manufacturer, substantially all oxygen concentrator systems require the use of an air intake filter for removing bacteria, environmental dust, and other particulates.

For proper operation and for the health and safety of the patients, the bacteria filters used in oxygen concentrator systems must be replaced periodically. Unfortunately, the structures and/or dimensions of the bacteria filters required for most models of oxygen concentrator will differ depending upon the manufacturer. Consequently, the design of the filter used in an oxygen concentrator system sold by one manufacturer will typically not be compatible with an oxygen concentrator system produced by a different manufacture. In addition, some oxygen concentrators require the use of bacteria filters which must be oriented vertically, while others require that the bacteria filter be oriented horizontally. Further, even with the same manufacturer, the bacteria filter used for an oxygen concentrator of one capacity (e.g., a five-liter unit) often will not be compatible with a concentrator of a different capacity (e.g., a ten-liter unit).

Health care facilities and others will commonly own multiple oxygen concentrators which were produced by different manufacturers and/or have different capacities. Similarly, the customers served by medical supply companies will typically have numerous different types of oxygen concentrator systems. Consequently, these facilities, suppliers, and others must order, keep track of, and maintain an adequate inventory of various different models of bacteria filters. If the user or supplier runs out of bacteria filters for a particular model of oxygen concentrator, the bacteria filters on hand for use in other models typically will not be compatible with the model in question.

Consequently, a need exists for a universal bacteria filter which (a) is compatible with substantially all models and sizes of oxygen concentrators, (b) can be oriented for either vertical or horizontal use, (c) is as effective, or more effective, than the various models of bacteria filters currently on the market, and (d) is competitively priced.

SUMMARY OF THE INVENTION

The present invention provides a universal bacteria filter apparatus which satisfies the needs and alleviates the problems discussed above. The all-in-one universal filter is adapted to replace multiple different filters with varying dimensions and configurations and to fit most of the oxygen concentrators in the market worldwide. Thus, the inventive universal filter eliminates the need to keep multiple different models of bacteria filters in stock. In addition, the inventive filter apparatus only weighs about 85 grams.

In one aspect, there is provided a filter apparatus for universal use in oxygen concentrators of different constructions. The filter apparatus preferably comprises: (a) a filter box having an interior, a first longitudinal end, a second longitudinal end opposite the first longitudinal end, and an open face which extends between the first longitudinal end and the second longitudinal end; (b) a discharge fitting which projects outwardly from the first longitudinal end of the filter box; (c) a cover which is removably positionable over the open face of the filter box; and (d) a plurality of filter elements which are removably receivable through the open face of the filter box for placement in the interior of the filter box. The filter elements preferably comprise at least (i) a first filter element which extends longitudinally in the interior of the filter box and (ii) a second filter element which is positioned in the interior of the filter box between a longitudinal end of the first filter element and the first longitudinal end of the filter box and is also perpendicular to the first filter element.

In another aspect, there is provided a filter apparatus for universal use in oxygen concentrators produced by different manufacturers, wherein the filter apparatus preferably comprises: (i) a filter box having an interior, a first longitudinal end, a second longitudinal end opposite the first longitudinal end, and an open face which extends between the first longitudinal end and the second longitudinal end; (ii) a discharge fitting which projects outwardly from the first longitudinal end of the filter box, the discharge fitting being a tubular segment having a distal discharge opening at a distal end of the tubular segment and a side discharge opening through a cylindrical side wall of the tubular segment; (iii) a cover which is removably positionable over the open face of the filter box; (iv) at least one filter element which is removably receivable through the open face of the filter box for placement in the interior of the filter box; and (v) a spout for converting the filter apparatus for use in a different orientation. The spout preferably comprises: (a) a cap which is receivable on the discharge fitting, the cap having a closed forward end and a cylindrical wall which extends rearwardly from the closed forward end and is receivable over the cylindrical side wall of the discharge fitting and (b) a side conduit segment which extends laterally outward from the cylindrical wall of the cap and has an inlet opening which is positionable over the side discharge opening of the discharge fitting.

Further objects, features, and advantages of the present invention will be apparent to those in the art upon examination of the accompanying drawings and upon reading the following Detailed Description of the Preferred Embodiments.

DETAILED DESCRIPTION OF THE PREFERRED EMBODIMENTS

Figure 1:
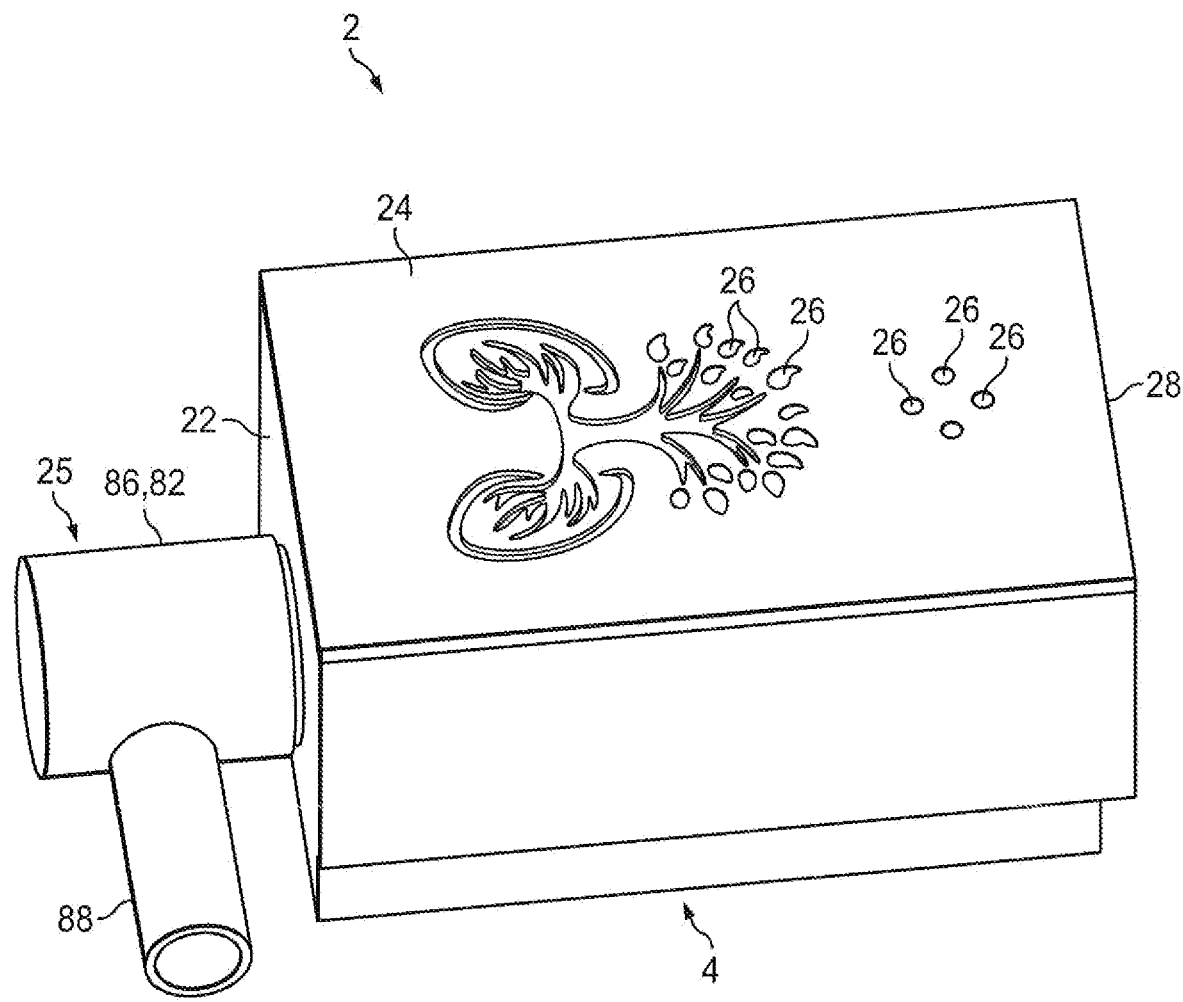
FIG. 1 is a perspective view of an embodiment 2 of the bacteria filter apparatus provided by the present invention.
Figure 2:
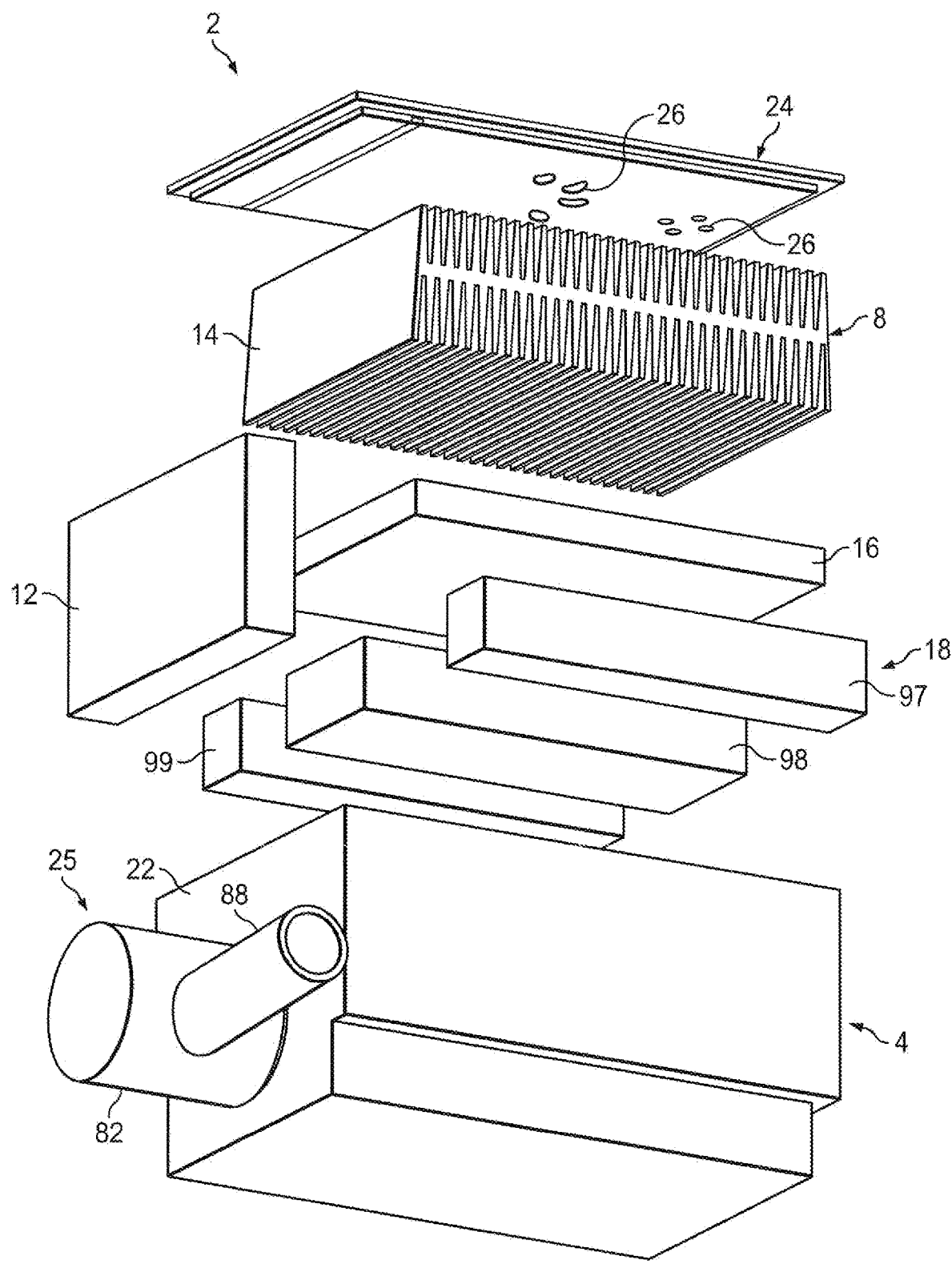
FIG. 2 is an exploded view of the inventive bacteria filter apparatus 2.
Figure 3:
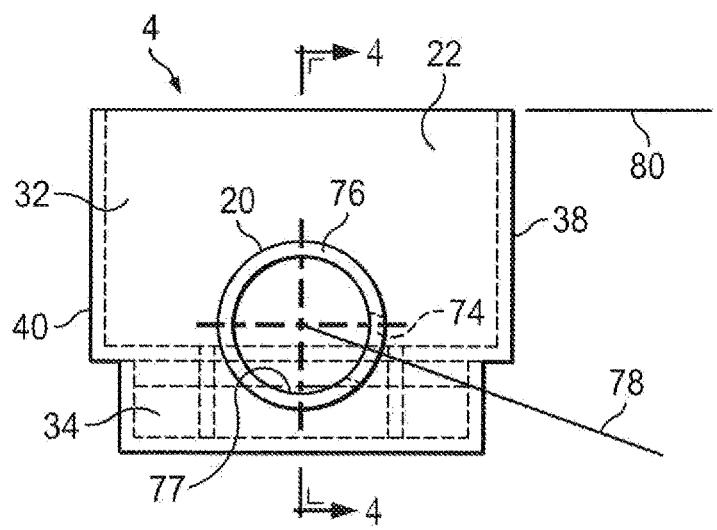
FIG. 3 is an end view of a filter box 4 used in the inventive apparatus 2.
Figure 4:
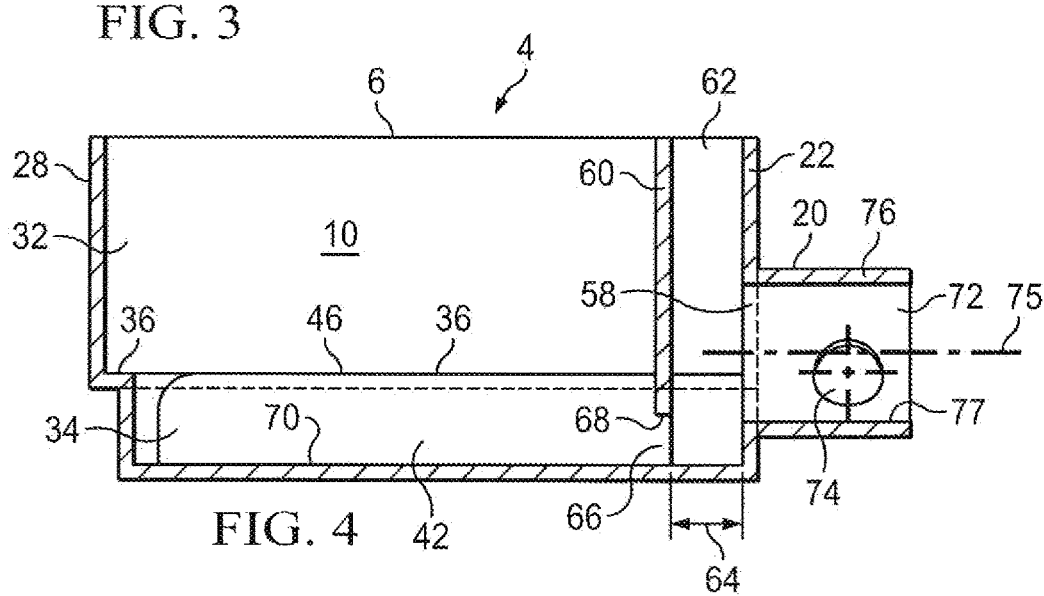
FIG. 4 is a cutaway side view of the filter box 4.
Figure 5:
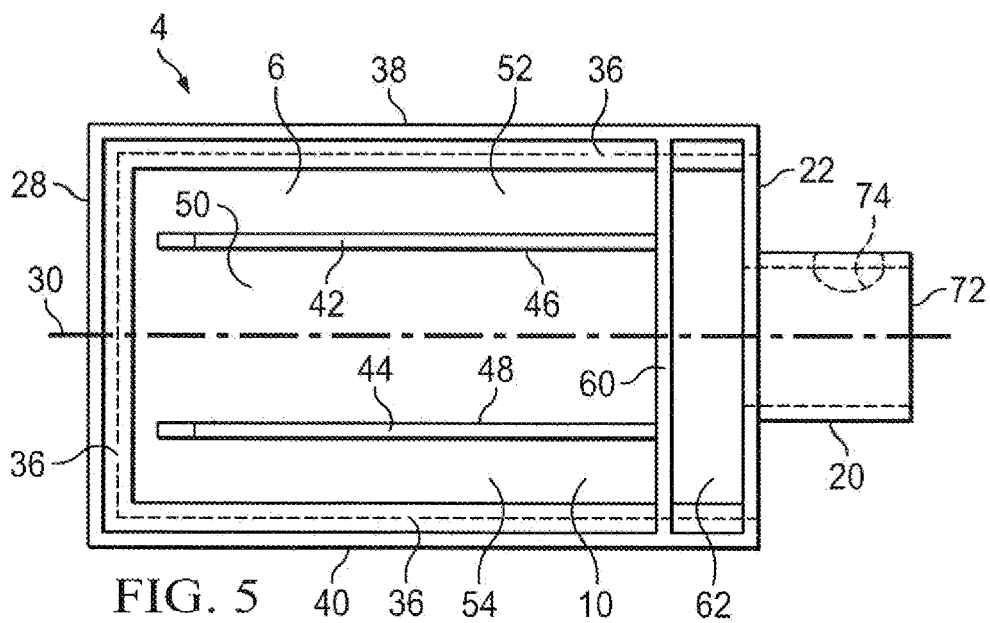
FIG. 5 is a top view of the filter box 4.
Figure 6:
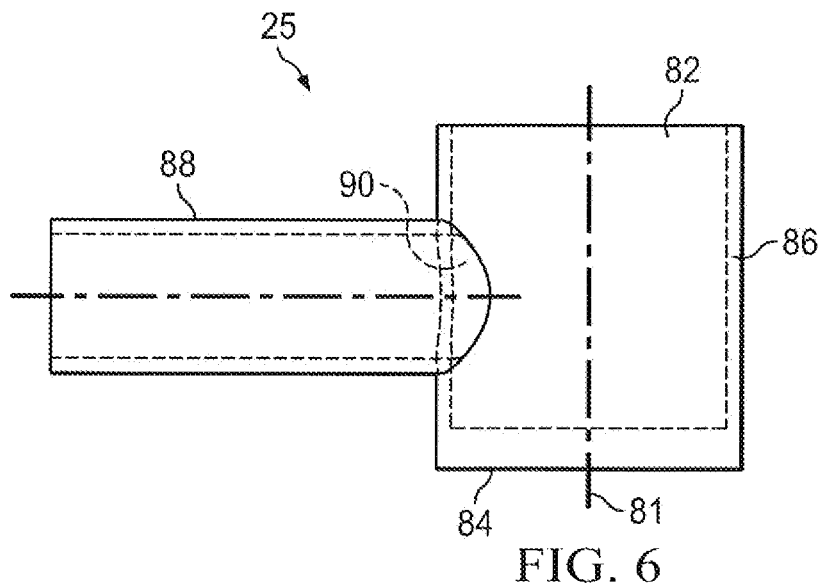
FIG. 6 is a top view of a removable spout 25 used in the inventive apparatus 2.
Figure 7:
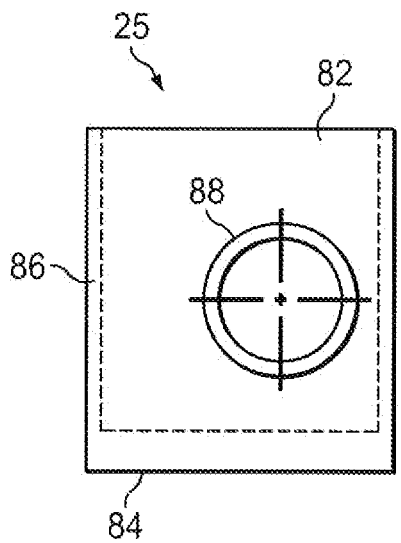
FIG. 7 is a side view of the spout 25.
Figure 8:
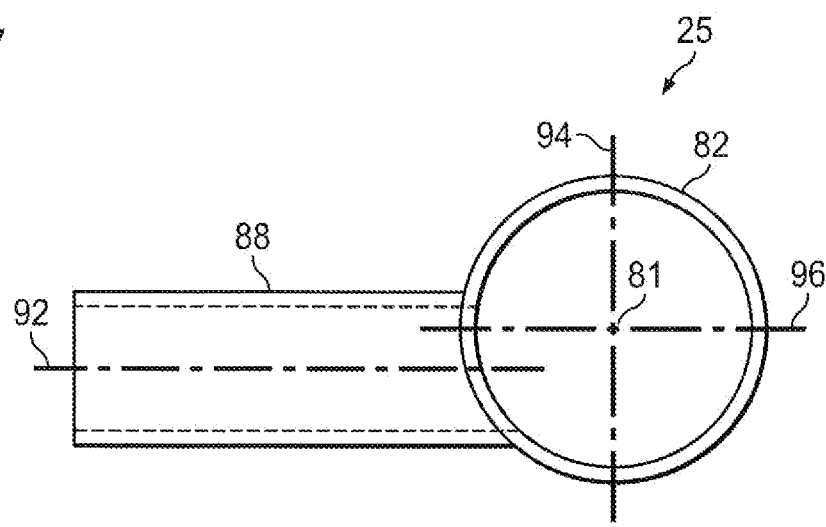
FIG. 8 is an end view of the spout 25.

An embodiment 2 of the inventive, all-in-one bacteria filter apparatus is illustrated in FIGS. 1-8. The inventive filter apparatus 2 preferably comprises: a filter box 4 having an open face 6 for receiving and removing filter elements; a first filter element 8 which extends longitudinally when positioned in the interior 10 of the filter box 4; a second filter element 12 which is perpendicular to a first longitudinal end 14 of the first filter element 8 when positioned in the interior 10 of the filter box 4; a third filter element 16 which is beneath and parallel to the first filter element 8, and perpendicular to the second filter element 12, when positioned in the interior 10 of the filter box 4; a segmented filter 18 which is beneath and parallel to the third filter element 16 when positioned in the interior 10 of the filter box 4; an exterior discharge fitting 20 of the filter box 4 which projects outwardly from a first longitudinal end 22 of the filter box 4; a cover 24 which is removably positionable over the open face 6 of the filter box 4 and has a plurality of air intake openings 26 therein; and a removable spout 25 for using the filter apparatus 2 in a horizontal orientation versus a vertical orientation.

When the inventive filter apparatus 2 is used in a vertical orientation, the open face 6 of the filter box 4 will typically be facing forwardly. When the inventive filter apparatus 2 is used in a horizontal orientation, the open face 6 of the filter box 4 will typically be facing upwardly. The open face 6 of the filter box 4 extends between the first longitudinal end 22 and the second (i.e., the opposite) longitudinal end 28 of the filter box 4.

The filter box 4 preferably comprises: a longitudinal axis 30; a longitudinally extended upper portion 32 of the box 4; a longitudinally extending lower portion 34 of the box 4 which is preferably slightly shorter and slightly narrower than the upper portion 32; an interior ledge 36 formed in the interior 10 of the filter box 4 on the second longitudinal end 28 and the two lateral sides 38 and 40 of the box 4; a pair of parallel, spaced apart, bottom support rails 42 and 44 which extend longitudinally through at least most of the longitudinal length of the lower portion 34 of the filter box 4, support rails 42 and 44 having longitudinally extending support edges 46 and 48 which are preferably substantially even with the interior ledge 36; a longitudinally extending central filter receiving track 50 formed in the lower portion 34 of the filter box 4 between the support rails 42 and 44; a first longitudinally extending outer filter receiving track 52 formed in the lower portion 34 of the filter box 4 outside of the support rail 42; a second longitudinally extending outer filter receiving track 54 which is formed in the lower portion 34 of the filter box 4 outside of the support rail 44; and an exterior discharge fitting 20 which projects outwardly from a discharge opening 58 in the first longitudinal end 22 of the filter box 4.

The filter box 4 also preferably comprises a lateral interior wall 60 which extends laterally across the interior 10 of the filter box 4 from the left side 38 to the right side 40 of the box 4. The lateral interior wall 60 is spaced apart from the first longitudinal end wall 22 of the filter box 4 to form a lateral filter receiving gap 62 between the lateral interior wall 60 and the first longitudinal end 22 of the box 4. The filter receiving gap 62 preferably has a longitudinal width 64 which is from 5% to 15%, more preferably from 8% to 13%, of the longitudinal length of the interior 10 of the longitudinally extending upper portion 32 of the filter box 4. The lateral interior wall 60 preferably extends downwardly from the open face 6 of the box 4 to a depth which is at or just above or just below the interior ledge 36 to form a bottom flow gap 66 between the laterally extending bottom edge 68 of the lateral interior wall 60 and the bottom surface 70 of the interior 10 of the filter box 4. The bottom edge 68 of the lateral interior wall 60 preferably extends into the longitudinally extending lower portion 34 of the filter box 4 such that the height 72 of the bottom flow gap 66 is preferably from 10% to 20%, more preferably from 12% to 17%, of the total depth of the interior 10 of the box 4.

The discharge fitting 20 of the filter box 4 is preferably a tubular segment which has a distal discharge opening 72 at the distal end of the tubular segment. The discharge fitting 20 also includes a side discharge opening 74 through the cylindrical side wall 76 of the tubular segment. The central longitudinal axis 75 of the discharge fitting 20, which is surrounded by the cylindrical side wall 76, will preferably be located at a height which is above the height of the interior ledge 36 of the filter box. However, the interior bottom point 77 of the tubular segment which forms the discharge fitting 20 will preferably be located at a height which is below the interior ledge 36.

When the inventive filter apparatus 2 is used in a vertical orientation, the suction fitting of the oxygen concentrator will typically fit directly over the discharge fitting 20 to receive filtered air which is discharged from the distal discharge opening 72 of the discharge fitting 20. When the inventive filter apparatus 2 is used in a horizontal orientation, the spout 25 is positioned over the discharge fitting 20 such that the filtered air travels through the spout 25 to the oxygen concentrator from the side discharge opening 74 of the discharge fitting 20.

The side discharge opening 74 of the discharge fitting 20 is preferably oriented such that a line 78 which extends from, and is perpendicular to, the longitudinal axis 75 of the discharge fitting 20 and extends through a center point of the side discharge opening 74 will be angled from 12° to 25°, more preferably from 16° to 23° away from a plane 80 which includes and is defined by the open face 6 of the filter box 4.

The spout 25 preferably comprises (a) a longitudinal axis 81, (b) a cap 82 which is removably receivable on the discharge fitting 20, the cap 82 having a closed forward end 84 and a cylindrical wall 86 which extends rearwardly from the closed forward end 84 and is receivable over the cylindrical side wall 76 of the discharge fitting 20, and (c) a side conduit segment 88 which extends laterally outward from the cylindrical wall 86 of the cap 82 and has an inlet opening 90 which is positionable over the side discharge opening 74 of the discharge fitting 20.

The side conduit segment 88 of the spout 25 has an inside diameter which is from 30% to 55%, more preferably from 35% to 50%, of the inside diameter of the cylindrical wall 86 of the cap 82. The side conduit segment 88 of the spout 25 preferably has a longitudinal axis 92 which (i) is perpendicular to a first plane 94 which includes the longitudinal axis 81 of the cylindrical wall 86 of the cap 82 and (ii) parallel to a second plane 96 which also includes the longitudinal axis 81 of the cylindrical wall 86 of the cap 82, wherein the second plane 96 is perpendicular to the first plane 94 and the longitudinal axis 92 of the side conduit segment 88 of the spout 25 is spaced a distance from the second plane 96 which is from 20% to 50%, more preferably from 25% to 40%, of the inside diameter of the side conduit segment 88 of the spout 25.

The first filter element 8 extends longitudinally in the interior 10 of the longitudinal upper portion 32 of the filter box 4 from (a) the lateral interior wall 60 to (b) the second longitudinal end 28 of the filter box 4. The first filter element 8 also has a width which extends from the lateral side 38 to the lateral side 40 of the filter box 4. The first filter element 8 is preferably a high efficiency particulate air (HEPA) filter. The first filter element 8 is most preferably a pleated, number 13, medical grade HEPA filter which is effective for removing dust, pollen, mold, bacteria, and other airborne particulates having a particle size of as small as 0.3 microns. The efficiency of the HEPA filter for removing such particulates will preferably be at least 99.8% and will more preferably be at least 99.97%.

The second filter element 12 is preferably formed of synthetic cotton, felt, or other material which is effective for particle removal and noise reduction and is most preferably a synthetic cotton filter. The second filter element 12 is removably inserted into the lateral filter gap 62 between the lateral interior wall 60 and the first longitudinal end 22 of the filter box 4 such that the second filter element 12 is perpendicular to the first longitudinal end 14 of the first filter element 8. The second filter element 12 extends laterally in the interior 10 of the filter box 4 from the lateral side 38 to the lateral side 40 of the box 4 and preferably extends downwardly from the open face 6 of the box 4 to a depth which is below the interior ledge 36 of the box 4 and below the bottom of the discharge fitting 20.

The longitudinal length and the lateral width of the third filter element 16 are preferably the same as those of the first filter element 8. The third filter element 16 is removably positionable in the interior 10 of the filter box 4 beneath the first filter element 8 such that the third filter element 16 extends longitudinally in parallel with the first filter element 8. The bottom of the third filter element 16 preferably rests on the interior ledge 36 and the bottom support rails 42 and 44 of the filter box 4. The third filter element 16 is preferably formed of synthetic cotton, felt, or other material which is effective for particle removal and noise reduction and will most preferably be a synthetic cotton filter.

The segmented filter 18 comprises three, side-by-side filter strips 97, 98, and 99 which are removably positionable in the longitudinal tracks 50, 52, and 54 formed in the bottom of the filter box 4 by the bottom support rails 42 and 44 such that the filter strips 97, 98, and 99 are positioned beneath the third filter element 16 and extend longitudinally from the lateral interior wall 60 to the second longitudinal end 28 of the longitudinally extending lower portion 34 of the interior 10 of the filter box 4. The filter strips 97, 98, and 99 are preferably formed of synthetic cotton, felt, or other material which is effective for particle removal and noise reduction and will most preferably be formed of synthetic cotton.

When operating as an air intake bacteria filter for an oxygen concentrator, the intake air received through the intake openings 26 of the cover 24 of the filter box 4 flows downwardly through the first filter element 8 and the third filter element 16 and into the segmented filter 18. The air then flows longitudinally toward and through the bottom flow gap 66 beneath the lateral interior wall 60. Next, the air flows upwardly through a lower portion of the second filter element 12 in the lateral filter gap 62 and then into the discharge fitting 20.

If the inventive filter apparatus 2 is installed in the oxygen concentrator system as a vertical filter, the filtered air will be directly discharged to the concentrator connection via the distal discharge opening 72 of the discharge fitting 20. Alternatively, if the inventive filter apparatus 2 is being used in the concentrator system in a horizontal orientation, the spout 25 will be positioned on the discharge fitting 20 of the filter box 4 and the filtered air will be delivered to the oxygen concentrator via the side discharge opening 74 of the discharge fitting 20 and the side conduit segment 88 of the spout 25.

The following example is provided to illustrate but in no way limit the scope of the present invention.

EXAMPLE

Two 5 liter, Invacare Perfecto2 Model oxygen concentrators were run side-by-side. One of the concentrators used the Invacare Perfecto2 bacteria filter which is specifically designed by the manufacturer for use with this concentrator system and the other concentrator used the inventive bacteria filter apparatus 2 described above wherein the first filter element 8 was a HEPA No. 13 medical grade filter and the second filter element 12, the third filter element 16, and the segmented filter 18 were all synthetic cotton filter elements.

The results of the side-by-side comparison were as follows:

| DATE | TIME | LITER FLOW L/S | OUTLET PRESS psi | 02 PURITY % |
|---|---|---|---|---|
| INVACARE PERFECTO2 | | S.N. 14FF031107 | | UNIVERSAL BACTERIA FILTER |
| Aug. 9, 2021 | 11:00 AM | 4.9 | 5.3 | 94.3 |
| Aug. 9, 2021 | 2:00 PM | 4.9 | 5.5 | 94.3 |
| Sep. 9, 2021 | 5:00 PM | 4.9 | 5.4 | 94.8 |
| Aug. 10, 2021 | 8:00 AM | 4.9 | 5.5 | 94.9 |
| Aug. 10, 2021 | 12:00 PM | 5 | 5.5 | 95 |
| Aug. 10, 2021 | 2:00 PM | 5 | 5.5 | 95 |
| Aug. 10, 2021 | 5:30 PM | 5 | 5.5 | 94.9 |
| Aug. 11, 2021 | 9:00 AM | 5 | 5.5 | 94.9 |
| Aug. 11, 2021 | 2:00 PM | 5 | 5.1 | 94.6 |
| Aug. 11, 2021 | 5:30 PM | 5 | 5.4 | 95.1 |
| Aug. 12, 2021 | 9:30 AM | 5 | 5.5 | 94.9 |
| Aug. 12, 2021 | 11:30 AM | 5 | 5.5 | 94 |
| INVACARE PERFECTO2 | | S.N. 15DFO31638 | | INVACARE PERFECTO2 BACTERIA FILTER |
| Aug. 9, 2021 | 11:00 AM | 4.9 | 5.4 | 94.2 |
| Aug. 9, 2021 | 2:00 PM | 4.9 | 5.3 | 94.4 |
| Sep. 9, 2021 | 5:00 PM | 4.9 | 5.2 | 94.5 |
| Aug. 10, 2021 | 8:00 AM | 5 | 5.2 | 94.4 |
| Aug. 10, 2021 | 12:00 PM | 5 | 5.2 | 94.2 |
| Aug. 10, 2021 | 2:00 PM | 5 | 5.5 | 94.8 |
| Aug. 10, 2021 | 5:30 PM | 4.9 | 5.2 | 94.5 |
| Aug. 11, 2021 | 9:00 AM | 4.9 | 5.2 | 94.4 |
| Aug. 11, 2021 | 2:00 PM | 4.9 | 5 | 94.2 |
| Aug. 11, 2021 | 5:30 PM | 5 | 5.2 | 94.4 |
| Aug. 12, 2021 | 9:30 AM | 5 | 5.4 | 94 |
| Aug. 12, 2021 | 11:30 AM | 4.9 | 5.5 | 94.1 |

As these results show, the flow rate, outlet pressure, and oxygen purity (i.e., the percent oxygen content of the concentrated oxygen product streams produce by the oxygen concentrators) were essentially the same or slightly better when using the inventive bacteria filter apparatus 2 versus the bacteria filter supplied by the manufacturer.

Thus, the present invention is well adapted to carry out the objects and attain the ends and advantages mentioned above as well as those inherent therein. While presently preferred embodiments have been described for purposes of this disclosure, numerous changes and modifications will be apparent to those in the art. Such changes and modifications are encompassed within this invention as defined by the claims.

What is claimed is:

1. A filter apparatus for universal use in oxygen concentrators of different constructions comprising:
   a filter box having an interior, a first longitudinal end, a second longitudinal end opposite the first longitudinal end, and an open face which extends between the first longitudinal end and the second longitudinal end;
   a discharge fitting which projects outwardly from the first longitudinal end of the filter box, the discharge fitting being a tubular segment having a distal discharge opening at a distal end of the tubular segment and a side discharge opening through a cylindrical side wall of the tubular segment;
   a cover which is removably positionable over the open face of the filter box;
   a plurality of filter elements which are removably receivable through the open face of the filter box for placement in the interior of the filter box, the filter elements comprising at least
      a first filter element which extends longitudinally in the interior of the filter box and
      a second filter element which (i) is positioned in the interior of the filter box between a longitudinal end of the first filter element and the first longitudinal end of the filter box and (ii) is perpendicular to the first filter element; and
   a spout for converting the filter apparatus for use in a different orientation, the spout comprising
      a cap which is receivable on the discharge fitting, the cap having a closed forward end and a cylindrical wall which extends rearwardly from the closed forward end and is receivable over the cylindrical side wall of the discharge fitting and
      a side conduit segment which extends laterally outward from the cylindrical wall of the cap and has an inlet opening which is positionable over the side discharge opening of the discharge fitting.

2. The filter apparatus of claim 1 further comprising:
   the discharge fitting having a longitudinal axis which is surrounded by the cylindrical side wall of the discharge fitting;
   the side discharge opening of the discharge fitting being oriented such that a line which extends from, and is perpendicular to, the longitudinal axis of the discharge fitting and extends through a center point of the side discharge opening is angled from 12° to 25° away from a plane which includes and is defined by the open face of the filter box;
   the side conduit segment of the spout having an inside diameter which is from 30% to 55% of an inside diameter of the cylindrical wall of the cap;
   the cylindrical wall of the cap having a longitudinal axis;
   the side conduit segment of the spout having a longitudinal axis which is perpendicular to a first plane which includes the longitudinal axis of the cylindrical wall of the cap;
   the longitudinal axis of the side conduit segment of the spout being parallel to a second plane, the second plane including the longitudinal axis of the cylindrical wall of the cap and the second plane being perpendicular to the first plane; and
   the longitudinal axis of the side conduit segment of the spout being spaced a distance from the second plane which is from 20% to 50% of the inside diameter of the side conduit of the spout.

3. The filter apparatus of claim 1 further comprising the first filter element being a HEPA filter.

4. The filter apparatus of claim 3 further comprising the second filter element being formed of synthetic cotton.

5. The filter apparatus of claim 3 further comprising the plurality of filter elements also including a third filter element which is positioned in the interior of the filter box beneath the HEPA filter and is perpendicular to the second filter element.

6. The filter apparatus of claim 5 further comprising the third filter element being formed of synthetic cotton.

7. The filter apparatus of claim 5 further comprising the filter box having a pair of parallel rails in the interior of the filter box beneath the third filter element, the pair of parallel rails running parallel to the HEPA filter.

8. The filter apparatus of claim 7 further comprising a segmented filter positioned in the interior of the filter box beneath the third filter element, the segmented filter comprising (i) an inner filter strip positioned in a track formed between the pair of parallel rails, (ii) a first outer filter strip which is positioned in a track outside of a first one of the pair of parallel rails and is parallel to the inner filter strip, and (iii) a second outer filter strip which is positioned in a track outside of a second one of the pair of the parallel rails and is parallel to the inner filter strip and the first outer filter strip.

9. The filter apparatus of claim 8 further comprising the inner filter strip, the first outer filter strip, and the second outer filter strip of the segmented filter being formed of synthetic cotton.

10. The filter apparatus of claim 1 further comprising the filter box including an interior wall which is positioned between the second filter element and the first longitudinal end of the first filter element, the interior wall being perpendicular to the open face of the filter box and to the first filter element, and the interior wall extending into the interior of the filter box from the open face of the filter box past the first longitudinal end of the first filter element.

11. The filter apparatus of claim 1 further comprising the cover having a plurality of air openings provided therethrough.

12. A filter apparatus for universal use in oxygen concentrators produced by different manufacturers comprising:
   a filter box having an interior, a first longitudinal end, a second longitudinal end opposite the first longitudinal end, and an open face which extends between the first longitudinal end and the second longitudinal end;
   a discharge fitting which projects outwardly from the first longitudinal end of the filter box, the discharge fitting being a tubular segment having a distal discharge opening at a distal end of the tubular segment and a side discharge opening through a cylindrical side wall of the tubular segment;
   a cover which is removably positionable over the open face of the filter box;

at least one filter element which is removably receivable through the open face of the filter box for placement in the interior of the filter box; and a spout for converting the filter apparatus for use in a different orientation, the spout comprising:

a cap which is receivable on the discharge fitting, the cap having a closed forward end and a cylindrical wall which extends rearwardly from the closed forward end and is receivable over the cylindrical side wall of the discharge fitting and a side conduit segment which extends laterally outward from the cylindrical wall of the cap and has an inlet opening which is positionable over the side discharge opening of the discharge fitting.

13. The filter apparatus of claim 12 further comprising:

the discharge fitting having a longitudinal axis which is surrounded by the cylindrical side wall of the discharge fitting;

the side discharge opening of the discharge fitting being oriented such that a line which extends from, and is perpendicular to, the longitudinal axis of the discharge fitting and extends through a center point of the side discharge opening is angled from 12° to 25° away from a plane which includes and is defined by the open face of the filter box;

the side conduit segment of the spout having an inside diameter which is from 30% to 55% of an inside diameter of the cylindrical wall of the cap;

the cylindrical wall of the cap having a longitudinal axis;

the side conduit segment of the spout having a longitudinal axis which is perpendicular to a first plane which includes the longitudinal axis of the cylindrical wall of the cap;

the longitudinal axis of the side conduit segment of the spout being parallel to a second plane, the second plane including the longitudinal axis of the cylindrical wall of the cap and the second plane being perpendicular to the first plane; and the longitudinal axis of the side conduit segment of the spout being spaced a distance from the second plane which is from 20% to 50% of the inside diameter of the side conduit of the spout.

14. The filter apparatus of claim 12 further comprising the filter element being a HEPA filter.

* * * * *